United States Patent [19]

Son et al.

[11] Patent Number: 5,239,071
[45] Date of Patent: Aug. 24, 1993

[54] PROCESS FOR METHYLATING A HINDERED NITROGEN ATOM IN AN INERT NON-AQUEOUS SOLVENT

[75] Inventors: Pyong-Nae Son, Akron; Victor L. Ledesma, Avon Lake; George Kletecka, Fairview Park, all of Ohio

[73] Assignee: The B. F. Goodrich Company, Akron, Ohio

[21] Appl. No.: 439,749

[22] Filed: Nov. 21, 1989

[51] Int. Cl.$^5$ .......................................... C07D 251/32
[52] U.S. Cl. ..................... 544/198; 544/113; 544/209; 544/212; 540/598
[58] Field of Search ............... 544/113, 198, 209, 212; 540/598

[56] References Cited

U.S. PATENT DOCUMENTS

| | | | |
|---|---|---|---|
| 4,190,571 | 2/1980 | Lai | 260/45.8 N |
| 4,480,092 | 10/1984 | Lai et al. | 544/113 |
| 4,629,752 | 12/1986 | Layer et al. | 524/100 |
| 4,639,479 | 1/1987 | Lai | 524/100 |
| 4,780,495 | 10/1988 | Lai | 524/100 |
| 4,816,507 | 3/1989 | Cantatore | 524/100 |

FOREIGN PATENT DOCUMENTS 2194237A 3/1988 United Kingdom ................ 544/113

OTHER PUBLICATIONS

Pine et al. J. Org. Chem. vol. 36, No. 6, 829-832 (1971).

Primary Examiner—Johann Richter
Attorney, Agent, or Firm—Alfred D. Lobo; Nestor W. Shust

[57] ABSTRACT

A process for methylating the $N^4$ atom of a polysubstituted piperazine or piperazin-2-one ("PSP") is effective despite using a much smaller molar excess of formaldehyde and formic acid than dictated by a conventional Eschweiler-Clarke reaction. Particularly in a complex amine in which the PSP substituent is connected to a triazine ring which in turn may be connected to a N atom of an acyclic polyamine, the molar ratio of NH groups:HCHO:HCOOH is in the range from about 1:1:1 to 1:1.5:1.5, the amount of HCHO and HCOOH being sufficient to methylate at least the >NH groups of said PSP substituent if the complex amine contains terminal —NH groups. The same range of molar ratio is maintained when the total number of NH groups to be methylated includes the terminal —NH groups. The effectiveness of the process is attributed to use of an alkylbenzene solvent in which reaction with only a slight excess of HCHO and HCOOH proceeds apace, and in which solvent the methylated product remains dissolved.

24 Claims, 1 Drawing Sheet

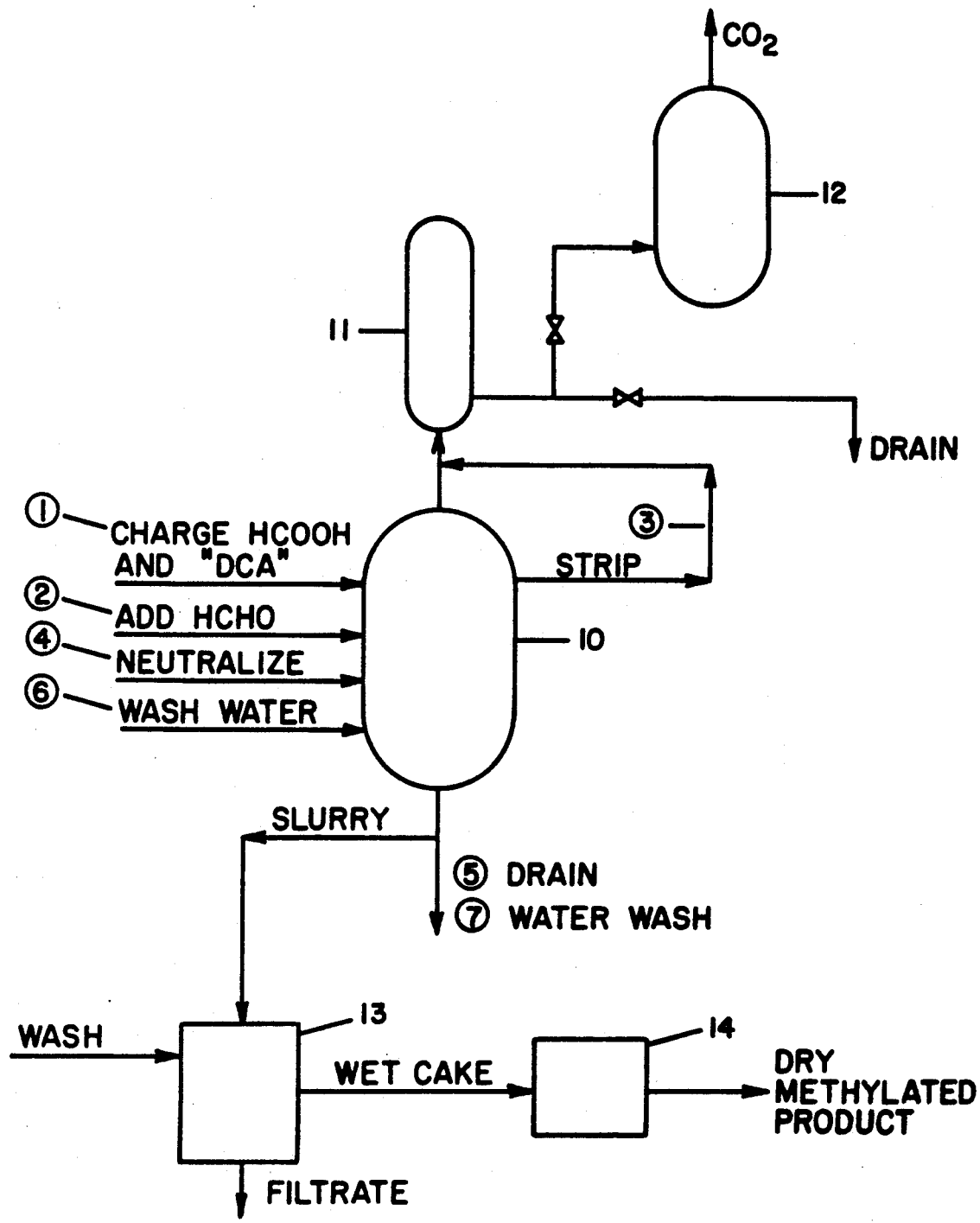

PROCESS FOR METHYLATING A HINDERED NITROGEN ATOM IN AN INERT NON-AQUEOUS SOLVENT

BACKGROUND OF THE INVENTION

This invention relates to a process for methylating a hindered nitrogen atom in the diazacycloalkane ring of a piperazine or piperazin-2-one which is substituted at both the 3- and 5- positions of the diaza ring. Such compounds are referred to as polysubstituted piperazine or piperazinone ("PSP" for brevity) compounds. The $N^4$ atom is hindered in all such PSPs. This $N^4$ atom is termed "the hindered N atom" because it is flanked by disubstituted 3- and 5-carbon atoms, either or both of which may have a spiro substituent. Compounds containing one or more PSP substituents are referred to as "PSP-substituted" compounds. An example of such compounds are triazine compounds having PSP substituents. The process of this invention is specifically related to the methylation of PSP-substituted triazine compounds. Methylated PSP-substituted triazine compounds are excellent stabilizers for polyoxymethylene resins, particularly polyacetals.

Hindered amines having a methylated hindered N atom, are highly desirable stabilizers for synthetic resinous materials, and command a premium price in the marketplace, whether the amine is a piperidine, piperazine or a piperazin-2-one derivative. Several methylated PSP stabilizers have been disclosed in Japanese patent application 63-86711 published Apr. 18, 1988. These stabilizers are said to improve the color of polyacetals though the PSPs are not connected to a triazine ring. There is no teaching of how such methylated compounds were prepared, but it is known that the high cost of producing the stabilizers confines their syntheses to the laboratory. Our process is directed to providing an economical solution to a difficult manufacturing problem.

The general process is described under the heading "Methylation of Amines with Formaldehyde" in Organic Reactions, Vol V by M. L. Moore, pg 307 et seq., as follows: One molecular proportion (or slight excess) of formaldehyde and two to four molecular proportions of formic acid are used for each methyl group introduced, indicating that it is mainly the formic acid that supplies the hydrogen involved in the reduction. The reaction is carried out on a steam bath. This variant of the Leuckart reaction is commonly known as the Eschweiler-Clarke ("E-C" for brevity) procedure.

The typical E-C reaction, carried out with a primary or secondary amine, results in the methylated amine only when heated for several hours after the evolution of gas has ceased due to reaction with an excess of formaldehyde and an excess of formic acid in an aqueous medium. The formic acid functions as both a co-reactant and a solvent. The function of formic acid as a solvent is particularly important when the amine to be methylated is poorly soluble in water.

Unhindered amines such as benzylamine and piperazine are expected to react to give almost theoretical yields of the corresponding tertiary amines. But in practice, they do not. It is therefore not surprising that hindered amines, which are are not expected to be essentially completely methylated by virtue of being hindered, should not be. The overall yield from the PSP-substituted triazine starting material is further reduced by the difficulty of recovering the desired product from the reaction mass ("work-up"). The result is substantially lower than theoretical yields from a high-priced starting material, and the low yields make the process uneconomic.

In a text-book procedure for a typical E-C reaction (see Moore, supra pg 323), benzylamine (1 mole) is added with cooling, to 5 moles of 90% formic acid. Then 2.2 moles of 35% formaldehyde solution is added, and the mixture is heated on a steam bath under reflux for 2 to 4 hours after evolution of gas has ceased (8 to 12 hr in all). Slightly more than 1 mole of concentrated hydrochloric acid is then added and the formic acid and any excess formaldehyde are evaporated on a steam bath. The colorless residue is dissolved in water and made alkaline by the addition of 25% aqueous sodium hydroxide, and distilled over sodium. The product, N,N-dimethylbenzylamine is recovered in about 80% yield. The unacceptability of such an yield in a commercial process is exacerbated by the very long time required for the reaction, time being an essential consideration in the economics of a process.

Despite the evident advantages of using water both as a solvent and as reaction medium, carrying out this reaction commercially is burdened with the costs of recovering the large excess of formaldehyde or formic acid, or both. For example, Czech appln. No. 82/5562 filed Jul. 21, 1982 discloses treating the methylated product with HCl, then distilling under vacuum to remove volatiles. The yield was 66-70% which is commercially unacceptable because of the high cost of PSP-substituted amine to be methylated. Such a distillation process still leaves the problem of separating the large excess of formic acid from the formaldehyde.

Separating formaldehyde and formic acid as aqueous solutions of chosen concentration (which may later be diluted) by distillation, is not practical because of the too-close boiling points. For example, USSR appln No. 80/22299, filed Oct. 10, 1980 discloses distillation in a column the pressure at the top and bottom of which was 20 mm and 2 atm respectively. Even if one was prepared to bear the cost of neutralizing formic acid, disposing of sodium formate solution is expensive; and one still has to deal with recovering, or disposing of the formaldehyde, for example by biological detoxification.

The foregoing general E-C procedure was followed with particular regard to a light stabilizer containing plural PSP substituents. UK Patent application GB 2194237A published Mar. 2, 1988, example 1 discloses preparation of a tetramine containing plural triazine rings, each substituted with two pentamethylated piperidyl substituents. The amine to be methylated is $N^1,N^2,N^3,N^4$-tetrakis-[2,4-bis[N-(2,2,6,6-tetramethyl-4-piperidyl)-n-butylamino]-1,3,5-triazin-6-yl]-4,7-diazadecane-1,10-diamine, and it has 8 tetramethyl-4-piperidyl substituents. To a solution of 0.02 moles of this amine in 100 ml of water is added 0.4 moles of formic acid and 0.4 moles of a 40% aqueous formaldehyde solution (each a 2-fold molar excess with terminal —NH groups). The solution is heated under reflux for 8 hr; after cooling to room temperature, an additional amount of 0.2 moles (stoichiometric) of 40% formaldehyde is added and the solution refluxed for an additional 5 hr.

In the foregoing E-C procedure, as in most of the Leuckart reactions, the reactions are carried out in the absence of any solvent other than the reagents themselves. However, nitrobenzene has been used as a solvent with a few ketones that were insoluble in the hot reaction mixture, and it has been used to increase the reflux temperature of reaction mixtures containing low boiling ketones (Moore, supra, bridging pgs 317-318).

In E-C reactions where the amine reactant is soluble in formic acid, and it is desired to keep the water to a minimum, essentially pure paraformaldehyde and the highest concentration of commercially available formic acid (above 95% HCOOH) is used, with no additional solvent added to the reaction mass. But such a reaction also requires a large excess of formic acid. The excess formic acid is difficult to recover and reuse. Addition of a non-aqueous solvent does not make recovery of the product and recovery of the formic acid easier. Hence, a commercial E-C process uses readily available aqueous solutions of formaldehyde and formic acid, and no additional solvent if the presence of water does not slow down the reaction too much. If economics require that the temperature at which the reaction proceeds be substantially higher than 100° C., a reactor must be maintained under substantially elevated pressure, which adds to the difficulty and cost of producing product.

Thus, given the practical necessity of using commercially available aqueous formic acid and formaldehyde, it would not seem that adding an additional solvent to the reaction system would serve any useful purpose. Particularly adding a water-immiscible solvent for the reactants and the methylated product would be at cross-purposes with the accepted function of water in the reaction since its function would be usurped by the solvent. Under such circumstances the duration of the reaction would be expected to be increased, not shortened. It could not have been foreseen that adding an alkylbenzene solvent would provide any significant benefit, either under "essentially dry" or essentially non-aqueous conditions, or under aqueous or "wet" conditions.

By "essentially dry" conditions we refer to a reaction mass which has less than 3% by weight (wt) water present after the reaction is complete and the reaction mass is essentially a single organic phase. The use of paraformaldehyde, or concentrated formaldehyde, and formic acid (85% HCOOH or higher), dictates that a little water be present, the amount of water increasing if the PSP or PSP-substituted reactant is moist (water not removed). By "wet" conditions we refer to a reaction mass in which there is at least 3% by wt water, but no more than about 30% by wt water, so that both aqueous and organic liquid phases are visually discernible. In either case, when the reaction is carried out at above about 60° C. $CO_2$ formed during the reaction is driven off. A higher temperature shortens the time for the reaction, producing the methylated tertiary amine, substantially quantitatively, typically in less than 8 hr.

Neither could it have been foreseen that, when the reaction is carried out in the presence of a sufficient amount of an alkylbenzene solvent to maintain the reactants in solution and provide less than 30% by weight of water in the reaction mass, the methylated product remains essentially completely in the alkylbenzene. This allows the reaction mass to be washed with water. By "solvent phase" we refer to the solution of organic material in the alkylbenzene solvent. This ability to wash out essentially all impurities from the solvent phase, including unreacted formaldehyde, formic acid and salt formed upon neutralization, enhances the efficiency of, and vastly simplifies the recovery procedure for the methylated product.

It will be evident from the foregoing, that the steps under which adequate conversion is obtained in a reasonable amount of time, and the steps of a work-up using a favorable partition coefficient under process conditions provided in the recovery system, must together provide an actual yield of essentially pure product high enough to make the process commercially successful.

Some of the foregoing considerations are indicated in a process for the methylation of triazine compounds containing 2,2,6,6-tetramethylpiperidine groups, disclosed by Piccinelli et al in European patent application 0319480 published June 6, 1989. The peculiar characteristics of triazine compounds containing such piperidyl groups requires that, if paraformaldehyde is substituted for 30-50% (weight/volume) aqueous formaldehyde, then the paraformaldehyde is suspended in water in a quantity necessary to obtain a $CH_2O$ concentration equal to 30-50%. Moreover, the reaction is carried out in the presence of aqueous alkali which almost completely eliminates $CO_2$ produced in the reaction.

Our process relates specifically to a modification of the well-known E-C procedure, which modification makes it possible to prepare PSPs and PSP-substituted compounds containing a methylated hindered N atom, on a commercial scale, economically. Our process is carried out in the presence of an inert organic liquid medium which is a solvent for the reactants and the desired methylated product, the solvent being chosen for its favorable partition coefficient for the methylated product in an aqueous system. The solvent is preferably an aromatic liquid such as an alkyl benzene chosen from ethylbenzene, trimethylbenzene, xylene, and most preferably toluene. The compound to be methylated is dispersed in the solvent and the reaction is carried out with a specified slight excess of paraformaldehyde and formic acid. Unlike an E-C methylation of piperidyl-substituted triazines, aqueous alkali is added only after the methylation reaction is complete, since the boost due to the reducing action of the alkali metal salt is not only unnecessary in our E-C reaction, it serves only to pre-neutralize formic acid. By "inert" we refer to a solvent which is unreactive with the compounds in the reaction mass under the conditions of the reaction.

SUMMARY OF THE INVENTION

It has been discovered that the hindered $N^4$ atom of a polysubstituted piperazine or piperazine-2-one ("PSP") may be methylated using a modified Eschweiler-Clarke ("E-C") procedure which requires carrying out the reaction under either "wet" or "essentially dry" conditions, in less formic acid than will form a solution with the PSP, so as to produce the $N^4$-methylated product in an alkylbenzene solvent which can be washed with water to obtain the methylated product in an yield in excess of 90%.

It is therefore a general object of this invention to provide a modification of the E-C procedure using aqueous formaldehyde or substantially anhydrous paraformaldehyde, and concentrated aqueous formic acid present in too small an amount to form a solution of the PSP or PSP-substituted complex amine to be methylated; the reaction is carried out under "wet" conditions in an alkylbenzene in which the methylated reaction product is soluble, at a temperature at which water formed during the reaction remains in the reaction mass, so that there are two liquid phases present; there is more alkylbenzene than water in the reaction mass; there is less than 1% by weight, of methylated PSP or PSP-substituted product in the aqueous phase; and, the yield of the methylated product is a least 90%.

It is another general object of this invention to provide a modification of the E-C procedure in which (a) solid paraformaldehyde is substituted for aqueous formaldehyde; (b) the amount of aqueous formic acid (at least 85% by weight HCOOH) is too small to dissolve the PSP or PSP-substituted compound to be methylated; (c) the reaction is carried out under "essentially dry" conditions at or below reflux temperature in an alkylbenzene in which both the amine reactant and the methylated reaction product are soluble, so that there is less than 3% by wt water present after reaction is complete; (d) the organic phase is then washed with water without transferring more than 5% by wt, preferably less than 1% by wt, of the methylated product to the aqueous phase; and, (e) the yield of the methylated amine is at least 90%, and preferably 95% or more.

It has further been discovered that the foregoing modifications of the E-C process, permit essentially quantitative yield of the methylated product and an accelerated rate of reaction at a sufficiently high temperature at or below the reflux temperature, so as to make the product made in less time than is required for an E-C process in which no alkylbenzene solvent is used.

It has also been discovered that a complex amine including a triazine ring with at least one PSP substituent (referred to as a "PIP-T" for brevity) has a peculiarly attractive partition coefficient in a mixture of an alkylbenzene ("solvent phase"), and water ("aqueous phase)". This coefficient allows the solvent phase to be washed with water to remove unreacted formaldehyde, formic acid and by-product impurities, yet transferring less than 1% by wt of the methylated PSP or PIP-T from the solvent phase to the aqueous phase. Therefore harvesting product from both phases is avoided.

It is therefore another general object of this invention to provide the foregoing modification of the E-C procedure in which the methylated PSP or PIP-T has such a favorable partition coefficient in an alkylbenzene relative to the aqueous phase, that the solvent phase may be washed with water with the loss of less than 1% of the theoretically formed methylated product being transferred from the solvent phase to the aqueous phase.

It is a specific object of this invention to provide the foregoing essentially dry process for the methylation in toluene, of a hindered N4 atom of a PIP-T (PSP-substituted triazine compound).

It is another specific object of this invention to provide the foregoing essentially dry E-C process wherein the molar ratio of the >NH group(s) in the PSP or PSP-substituted compound, paraformaldehyde, formic acid (at least 85%) is in the range from about 1:1:1 to about 1:2:2, preferably in the range from 1:1.02:1.02 to 1:1.5:1.5, and most preferably from 1:1.05:1.05 to 1:1.2:1.2, and the reaction is carried out in toluene.

It is still another specific object of this invention to provide the foregoing essentially dry E-C process for the methylation of each hindered $N^4$ atom of a PIP-T, in which process less than a 0.5 molar excess of formate is precipitated by the addition of alkali, but the methylated PIP-T remains in solution in an alkylbenzene solvent having a partition coefficient such that the solution can be washed with water without removing more than 1% of the methylated product with the wash water.

It is yet another specific object of this invention to provide the foregoing essentially dry E-C process for the methylation of each hindered $N^4$ atom in a PIP-T, the process being carried out in an oxygen-free reaction zone operating at relatively low, preferably autogenously developed pressure at the temperature of reaction, in toluene.

It is a further specific object of this invention to provide the foregoing essentially dry E-C process for the methylation of a PIP-T, the process being carried out in a reaction zone operating (a) at or below the boiling point of an azeotrope of toluene or xylene and autogeneous pressure, (b) with about twice as much by wt of alkylbenzene solvent as methylated product to be formed; thereafter (c) neutralizing the solvent phase in the reaction zone only after the methylation reaction is complete, without precipitating the metylated product; (d) separating and washing the solvent phase with water, yet removing (in the water) less than 1% by weight of the product theoretically formed; (e) concentrating the solvent phase; and (f) precipitating the product from the concentrated solution by adding a sufficient amount of a liquid alkane to obtain at least a 90% yield of methylated product.

BRIEF DESCRIPTION OF THE DRAWINGS

The foregoing and other objects and advantages of our invention will appear more fully from the following description, made in connection with the accompanying flowsheet of a preferred embodiment of the invention, illustrating a single multi-purpose reactor and associated equipment, in which reactor a PSP or PIP-T is methylated in an alkylbenzene solvent.

DETAILED DESCRIPTION OF PREFERRED EMBODIMENTS

It will now be evident that use of the appropriate alkylbenzene solvent, present in a major amount by weight relative to water, and preferably in a ratio of alkylbenzene:water >2, permits the essentially complete conversion of the PSP or PSP-substituted compound (e.g. a PIP-T) to be methylated with the specified small molar excesses of formaldehyde and formic acid. This is attributable to the unique characteristics of the polysubstituted diazacycloalkane or diazacycloalkan-2-one ring of compounds disclosed in U.S. Pat. No. 4,190,571 to Lai and Son, the disclosure of which is incorporated by reference thereto as if fully set forth herein. What is also evident is that, because the reaction mass must be water-washed, the choice of the organic solvent would be very difficult without knowing that an alkylbenzene solvent would not only be an excellent solvent for both the amine reactant and the methylated product, but also that it would provide at least a 0.90, and preferably a 0.99 partition coefficient for the methylated product in water.

The general structure of a polysubstituted diazacycloalkane or polysubstituted diazacycloalkan-2-one which is so effectively methylated in our process is represented by

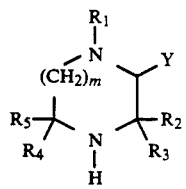
(I)

wherein, m represents an integer in the range from 1 to 6, being the number of methylene groups some of which, (a) together with the carbons to which they are bound, may form a cyclopentyl, cyclohexyl or cycloheptyl endo ring, or (b) be substituted;

Y represents H or =O (oxygen), and when Y is 0 and m is 1 then (I) represents a polysubstituted piperazin-2-one moiety, and when Y is 0 and m is 5, and two of the methylene groups of the diaza ring are cyclized with four methylene groups to form a fused six-membered ring, then (I) typically represents a polysubstituted 2-keto-decahydroquinoxaline;

$R_1$ independently represents hydrogen, $C_1$–$C_{24}$ alkyl, $C_1$–$C_{12}$ aminoalkyl or iminoalkyl, and $C_1$–$C_{12}$ hydroxyalkyl; and when (I) is a substituent, $R_1$ represents a bond to an amine;

$R_2$, $R_3$, $R_4$ and $R_5$ independently represent $C_1$–$C_{24}$ alkyl; and, $R_2$ with $R_3$, or $R_4$ with $R_5$, together cyclized, form $C_5$–$C_7$ cycloalkyl.

The best mode of our process relates to methylation of PIP-Ts such as those disclosed in U.S. Pat. Nos. 4,480,092; 4,629,752; 4,639,479. At least the hindered $N^4$ atom of each NH group, and preferably every other terminal —NH group in each PSP-substituted compound is to be methylated.

PIP-Ts are typically prepared by substituting at least one, and most preferably, each of two or three chlorine (or other halogen) atoms on a di- or trihalo-s-triazine, specifically cyanuric chloride, with a PSP, so as to form a substituted triazine. Such PIP-T compounds in which the diazacycloalkane ring is connected to the triazine ring through an alkyleneimine linkage (hence termed "distally connected"), are identified more fully herebelow for illustrative purposes, and in the foregoing '092, '752 and '479 patents.

A preferred substituted triazine is represented by the structure

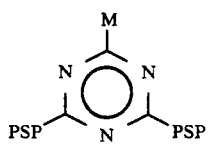
(II)

wherein PSP represents a substituent selected from the group consisting of structures

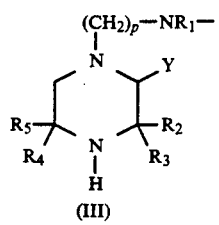 and 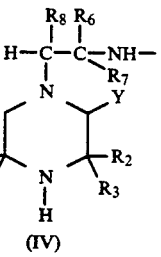
(III) (IV)

wherein, Y represents H or =O;
$R_1$ represents $C_1$–$C_{24}$ alkyl, $C_5$–$C_{12}$ cycloalkyl, phenyl, $C_7$–$C_{20}$ aralkyl, $C_1$–$C_{24}$ azaalkyl, and $C_6$–$C_{20}$ azacycloalkyl; $R_2$, $R_3$, $R_4$, and $R_5$ independently represent $C_1$–$C_{24}$ alkyl; $R_6$, and $R_7$ independently represent $C_1$–$C_{24}$ alkyl and polymethylene having from 4 to 7 C atoms which are cyclizable; and, p represents an integer in the range from 2 to about 10;

$R_8$ represents H, $C_1$–$C_6$ alkyl and phenyl; and, M may be the same as PSP or a bond to the N atom of an amine.

Other preferred PIP-Ts are represented by structures:

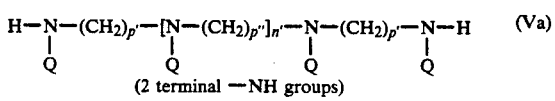
(Va)
(2 terminal —NH groups)

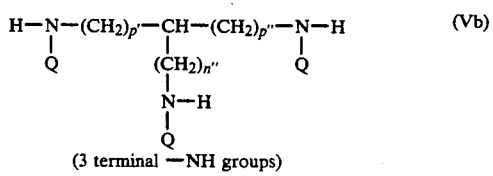
(Vb)
(3 terminal —NH groups)

and

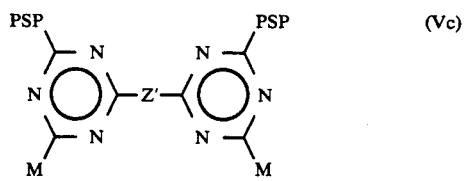
(Vc)

wherein n' represents an integer from 0 to 6; n" is 0 or 1;

p' and p" independently represent an integer in the range from 2 to about 20; and, Q represents

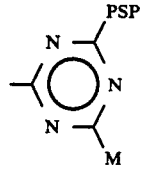

Z' represents

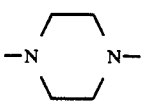

or —HN—$(CH_2)_p$—NH—

M represents —N(Bu)$_2$ where Bu=butyl,

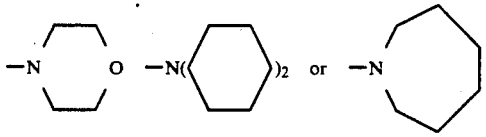

and, M may be the same as PSP.

A particular PIP-T is formed by the reaction of cyanuric chloride with a particular PSP amine reactant, 1-[3-(cyclohexylamino)propyl]-3,3,5,5-tetramethylpiperazin-2-one, familiarly referred to as cyclohexyl-piperazinone, ("CHP" for brevity), represented by the structure:

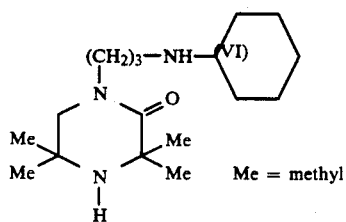

The structure of the PIP-T heterocylic amine which is to be methylated is represented as follows:

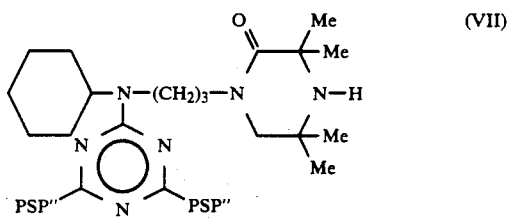

wherein PSP" represents the same structure written for the other substituent.

The structure of the desired methylated PIP-T product is represented as follows:

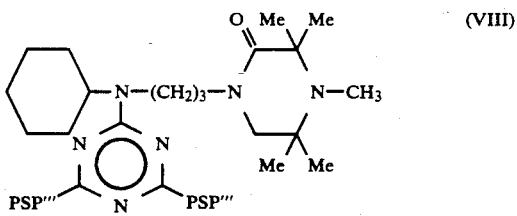

wherein PSP'" represents the same structure written for the other substituent.

Crystallizable triazines with other PSP moieties as substituents, whether di or tri-substituted, may also be methylated as described. The PIP-Ts are formed by reaction of cyanuric chloride with the following polysubstituted piperazin-2-ones:
1-[3-(isopropylamino)propyl]-3,3,5,5-tetramethylpiperazin-2-one;
1-[2-(isopropylamino)ethyl]-3,3,5,5-tetramethylpiperazin-2-one;
1-[2-(butylamino)ethyl]-3,3,5,5-tetramethylpiperazin-2-one; and,
1-[2-(cyclohexylamino)ethyl]-3,3,5,5-tetramethylpiperazin-2-one; inter alia.

In an analogous manner, PIP-Ts, whether di- or tri-substituted, may be formed by reaction of cyanuric chloride with the following polysubstituted piperazines:
1-[3-(isopropylamino)propyl]-3,3,5,5-tetramethylpiperazine;
1-[2-(isopropylamino)ethyl]-3,3,5,5-tetramethylpiperazine;
1-[2-(butylamino)ethyl]-3,3,5,5-tetramethylpiperazine; and,
1-[2-(cyclohexylamino)ethyl]-3,3,5,5-tetramethylpiperazine.

Prior art E-C Procedure

The processing aspects of the invention will be more fully recognized in a comparison with the conventional E-C procedure for methylating a PIP-T compound which procedure is as follows:

PIP-T + formaldehyde + formic acid ⟶ methylated PIP-T
0.6 mole      2.16 moles      6.48 moles              0.6 mole To a 5 liter reactor is charged 289 g (0.3 mole) PIP-T, 64.9 g of formaldehyde (in 37% solution) and 313.9 g of formic acid (in 90%). The mixture is heated to 65° C. with stirring and when the temperature reaches about 80° C., the remaining PIP-T is added. The temperature of the reaction mass is raised to about 102° C. and the reaction monitored by liquid chromatographic (LC) analysis, to monitor the disappearance of the PIP-T. Since there is a substantial amount of PIP-T remaining after 8 hr, the reaction is continued until essentially all the PIP-T has disappeared, about 12 hr.

The reaction mass obtained is a colored oil which, when cooled to room temperature, is highly viscous. To precipitate the methylated product from this oil, it is heated to about 80° C. and 1 liter of water added to obtain a slurry having a pH of about 3. When this slurry is neutralized with a large excess of 25% NaOH solution, a foamy solid is precipitated.

To work up this solid, the neutralized solution is filtered. The aqueous filtrate contains a substantial amount of VIII which does not precipitate. The white filter cake (965 g) is washed with about 2 liter of demineralized (DM) water in a 5 liter flask, and filtered.

After repeated washing to remove formaldehyde and formic acid, the washed cake is dried to yield 478 g of essentially pure methylated product. Since theoretical yield is 604.2 g it is necessary to recover the product remaining in both the aqueous alkaline filtrate as well as the first water wash.

The filtrate and water wash are heated with an additional amount of 25% NaOH to precipitate more solid which is washed and dried as before, to yield 102 g of product. Though recovery of 580 g of product represents a yield of 6%, it is essential to harvest two crops of product, one from the cake precipitated after neutralization of the E-C reaction mass, the other from the filtrate.

E-C procedure in a solvent medium: Essentially Dry Process

The modified E-C procedure for methylating the PIP-T VII is illustrated in a typical pilot plant run as follows:

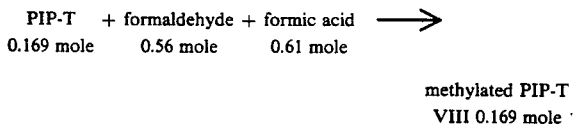

PIP-T + formaldehyde + formic acid ⟶
0.169 mole    0.56 mole    0.61 mole methylated PIP-T
VIII 0.169 mole The paraformaldehyde $HO(H_2CO)_nH$ used is 96% commercial grade which contains about 4% water; the formic acid used is 90% commercial grade; and the PIP-T having the structure VII is essentially pure and dry. The preferred molar ratio of NH groups in the PIP-T:HCHO:HCOOH is in the range from about 1:1.02:1.02 to 1:1.1:1.2. The percent excess (used in this run for methylating VII) over stoichiometric of paraformaldehyde is 10%, and of HCOOH is 20%. The amount of toluene added is such that the weight ratio of toluene to methylated product (to be theoretically formed) is in the range from about 2 to about 4, depending upon the solubility of the product in toluene, and for methylated PIP-T VIII is preferably in the range from about 2 to about 2.75. Toluene is favored for methylating VII but another alkylbenzene may be chosen for another PIP-T, particularly one represented by structures Va or Vb.

Into a glass-lined jacketed reactor provided with an agitator, a reflux condenser, and appropriate equipment adapted to carry out the reaction, is charged 350 lb of toluene and 160 lb of PIP-T VII and while stirring, purge oxygen by alternating a vacuum and blowing in nitrogen under about 30 psig pressure to ensure an oxygen-poor atmosphere. The contents are heated to 80° C. and while stirring, 31.12 lb 90% pure formic acid are gradually added while maintaining the temperature, so that the carbon dioxide evolved maintains an inert gas blanket before it is vented. The feed tank is rinsed with another 30 lb of toluene which is added to the reactor. The temperature is raised to 85° C. and the reaction completed at this temperature under total reflux, while making periodic LC analyses to determine when all the PIP-T VII has disappeared. The reaction is complete in about 2.5 hr.

The reaction mass is then cooled to 60° C., and enough aqueous 25% NaOH or $NH_4OH$ is added to neutralize the excess formic acid. If alkali is added before the reaction is complete, the amount of formic acid in the reaction mass is depleted and serves to slow rather than accelerate the desired reaction. The water phase is separated and discarded since its concentration of methylated PIP-T in the water phase is less than 1%, and more preferably less than 0.1% of theoretically produced product. Recovery of methylated product from the water phase is neither necessary nor economically justified. The formaldehyde and sodium (or ammonium) formate are also present, but in too low an amount to be economically recoverable, yet low enough a concentration to be biodegradable. The toluene phase is washed with hot DM water several times, mixing thoroughly for a period of 15 min each time at 50°-60° C., before settling.

The washed toluene solution is stripped to concentrate it until less than half the toluene remains. To this concentrated slush of the methylated PIP-T in toluene is added enough cool heptane to precipitate solid methylated product, forming a slurry. The slurry is centrifuged, and washed with more heptane in the centrifuge, before the cake is removed and dried. The filtrate from the centrifuge is recovered for reuse. The essentially pure methylated PIP-T VIII recovered is found to be more than 95% by weight of theoretical, illustrating that use of toluene as a solvent permits obtaining more than 95% of theoretical product, economically, in a single harvest from the reaction mass.

The reaction may be carried out at substantially atmospheric pressure below reflux temperature but above about 60° C., but the lower temperature will prolong the time required to complete the reaction. The reaction may be carried out under elevated pressure in the range from 2 to about 5 atm at the reflux temperature of the alkylbenzene solvent, or the azeotrope (the toluene-water azeotrope refluxes at about 84° C. at substantially atmospheric pressure) to speed up the reaction. To speed up the reaction further, water may be removed from the azeotrope and the toluene returned to the reactor. The reaction may then be continued at the boiling point of the solvent (about 110° C. for toluene). The reaction may be carried out at as high a temperature as will produce a tolerable amount of byproducts. Higher temperatures, if desired, may be obtained with an appropriate choice of solvent. A temperature above 150° C. will generally be too high to maximize the production of methylated product.

E-C procedure in a solvent medium: Wet Process

In a manner analogous to that described hereinabove, methylation of the PIP-T VII is carried out under "wet" process conditions using the same molar quantities of reactants, except that the PIP-T solids to be methylated are wet (containing from 30% to 60% water), and 37% formaldehyde and 90% formic acid are used so that the amount of water in the reaction mass is about 26% by weight (after the reaction is complete). The amount of toluene added is enough to give a toluene:product ratio of about 2.3. The reaction is carried out under total reflux, at the reflux temperature of the toluene-water azeotrope, the higher temperature being used to speed up the reaction. Progress of the reaction is monitored as before, and the reaction is complete in about 12 hr.

The reaction may be carried out under more dilute conditions, but serves no economic purpose since the presence of additional water and toluene serves to decrease the productivity (pounds product/unit volume of reactor) of the process.

The reaction mass is cooled, neutralized and worked up as before. Less than 1% by weight of the methylated product is lost in the water, and the yield of recovered product is greater than 95%.

The process is schematically illustrated in the Figure in which a reaction vessel 10 provides a reaction zone for obtaining essentially complete conversion of the PIP-T after the reactants are in solution in the solvent introduced. The first step in which the PIP-T, paraformaldehyde, formic acid and toluene are charged, is identified by reference numeral 1 written in a circle to distinguish the symbol from numerals used to identify equipment. In the "essentially dry" process, the PIP-T may be charged as an essentially dry powder, or as a toluene-wet cake or slurry, or as a solution in toluene, or other alkylbenzene solvent used, since the PIP-T must be in solution when it is methylated. In the "wet" process, the PIP-T may be charged as a water-wet cake, or a slurry in water, since a small amount of water, most preferably about 10% or less, does not prolong the time for methylation unacceptably.

After the reaction is complete, neutralization of the contents of the reactor either with a solution of an alkali metal hydroxide or ammonium hydroxide (identified as step 2), results in an aqueous layer which is conveniently drained (step 3) from the reactor. The solution of methylated PIP-T in alkylbenzene, specifically toluene, is washed with distilled water, several times if necessary, to remove formate and unreacted paraformaldehyde, and any water-soluble byproducts which may be formed. The wash water is drained from the reactor in step 4.

Toluene is then stripped (step 5) from the washed toluene phase, until a super-saturated solution remains. Toluene is withdrawn from the reflux condenser 11 into a condensate receiver 12 for later reuse. A surge tank 13 is provided for safety reasons.

The methylated PIP-T is then precipitated from the super-saturated solution, for example by cooling the hot super-saturated solution. This method is referred to as "direct precipitation". As an alternative, a precipitating agent is added, this method being referred to as "assisted precipitation".

As shown in the Figure, concentration of the solution of methylated PIP-T in toluene, precipitation of the methylated PIP-T, and washing out the unreacted formaldehyde, formic acid and impurities, are done in the reactor to avoid transferring the contents of the reactor, after the reaction is completed, to another vessel(s) for "workup" and recovery of the essentially pure methylated PIP-T.

It is preferred to use the reactor solely for carrying out the methylation reaction, and to work-up the solution of methylated PIP-T in toluene, after the reaction, in separate unit operations.

It is preferred to concentrate the solution in a "toluene still" and to precipitate the methylated PIP-T in a precipitation tank. The methylated PIP-T may not always be a crystalline solid, though the compound VIII is. The particular choice of precipitating agent depends upon how poor a solvent it is for a specific methylated PIP-T, providing of course the precipitating agent is miscible with the alkylbenzene By "miscible" is meant that the precipitating agent and alkylbenzene form a single liquid phase. Some methylated PIP-Ts represented by structures Va, Vb and Vc are essentially insoluble in acetone, methylethyl ketone, or another $C_1$–$C_{12}$ alkyl ketone, one of which may provide a satisfactory precipitating agent.

In the specific instance where VIII is to be recovered from a solution in toluene, addition of heptane to the super-saturated solution of VIII in toluene (step 6), precipitates VIII. Typically, a large amount of heptane is used, this amount (by wt) being substantially greater than the weight of toluene, preferably 2 to 10 times more heptane than toluene, so as to form a slurry of solid VIII in a heptane rich mixture of heptane-toluene.

The slurry of VIII in the heptane-toluene mixture is flowed to a centrifuge 14, in which the centrifuged solids are washed with successive washes of heptane to free the cake from toluene. The filtrate (or "centrate") from the centrifuge is recovered for reuse. The cake from the centrifuge is then dried in a vacuum oven 15, but, because of the extreme solubility of VIII in toluene, typically still contains more than about 100 ppm but less than 1% by wt of toluene. This dried product, essentially free of alkylbenzene solvent, is then transferred to suitable containers.

Irrespective of which specific process (dry or wet) is used, it may be desirable to finish the reaction at a higher temperature than that afforded by the toluene-water azeotrope (in the above example) without substantially increasing the operating pressure above atmospheric. This finishing step of the reaction, at a relatively higher temperature than the beginning of the reaction, is particularly useful when some of, or all the terminal —NH groups of the complex amine (PIP-T) are to be methylated.

In the specific instance when toluene is used, as shown in the Figure, water is decanted from the reflux condenser and toluene from the condensate receiver 12 is returned to the reactor. Higher reaction temperatures may be necessary with PIP-Ts other than the one used in the foregoing example, and may be obtained with xylenes as the solvent. An analogous finishing step, eliminating the water boiled off with the xylenes, and returning the xylenes to the reactor, may be used to methylate the terminal -NH groups of those complex amines which require a higher temperature to be methylated.

We claim:

1. A process for methylating a complex amine, specifically a triazine ring substituted with a polysubstituted piperazine or polysubstituted piperazin-2-one ("PSP") substituent, comprising, (a) reacting (i) said complex amine having at least one PSP substituent, each said substituent having a hindered $N^4$ atom flanked either by disubstituted carbon atoms, or carbon atoms having spiro substituents, with (ii) formaldehyde or paraformaldehyde, and (iii) formic acid in amounts such that the molar ratio of NH groups:HCHO:HCOOH is in the range from about 1:1:1 to 1:1.5:1.5 sufficient to methylate at least the >NH group of said PSP substituent if said complex amine also contains terminal —NH groups, so as to obtain essentially quantitative conversion of said PSP substituent to methylated PSP-substituent in said complex amine;

(b) adding a sufficient amount of an alkylbenzene solvent to maintain the reactants in solution, yet upon completion of the reaction, to have less than 30% by weight of water in the reaction mass, (c) maintaining a temperature above about 60° C. but below a temperature at which more than 10% by weight of said complex amine is converted to by-products, so as to form a solution of methylated complex amine in said alkylbenzene solvent;

(d) neutralizing unreacted formic acid with an aqueous alkaline solution without precipitating methylated product;

(e) separating an aqueous phase of neutralized formic acid from said solution of methylated complex amine;

(f) washing water-soluble impurities from said solvent phase;

(g) precipitating a solid mass of said methylated complex amine; and, (h) recovering said methylated product in essentially pure form, in an yield in excess of 90%.

2. The process of claim 1 wherein said complex amine contains terminal —NH groups and said molar ratio is based on the sum of >NH and —NH groups present in said amine.

3. The process of claim 2 wherein said complex amine is a heterocyclic amine represented by a structure selected from the group consisting of

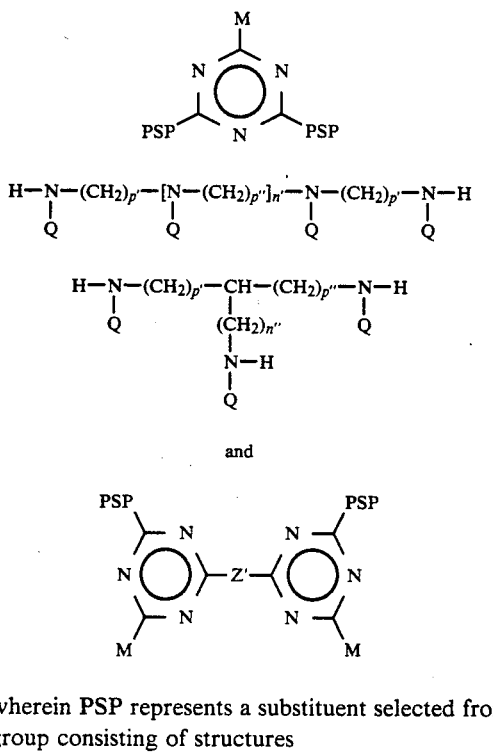

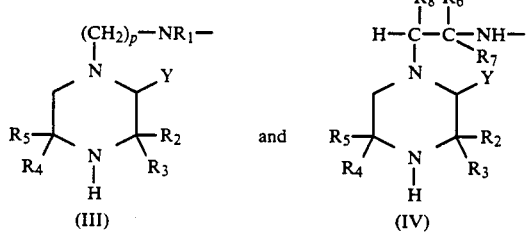

wherein PSP represents a substituent selected from the group consisting of structures

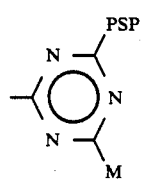

wherein, Y represents H or =O; $R_1$ represents $C_1$-$C_{24}$ alkyl, $C_5$-$C_{12}$ cycloalkyl, phenyl, $C_7$-$C_{20}$ aralkyl, $C_1$-$C_{24}$ azaalkyl, and $C_6$-$C_{20}$ azacycloalkyl; $R_2$, $R_3$, $R_4$, and $R_5$ independently represent $C_1$-$C_{24}$ alkyl; $R_6$, and $R_7$ independently represent $C_1$-$C_{24}$ alkyl and polymethylene having from 4 to 7 C atoms which are cyclizable; $R_8$ represents H, $C_1$-$C_6$ alkyl and phenyl; and, M may be the same as PSP or a bond to the N atom of an amine;

n' is an integer from 0 to 6; n" is 0 or 1;

p represents an integer in the range from 2 to about 10;

p' and p" independently represent an integer in the range from 2 to about 20;

Q represents

—N⟨piperazine⟩N— or —HN—(CH₂)ₚ—NH—

M represents —N(Bu)₂ where Bu=butyl,

—N⟨morpholine⟩O  —N(⟨cyclohexyl⟩)₂  or  —N⟨azepane⟩ and, M may be the same as PSP.

4. The process of claim 3 wherein precipitating said methylated PIP-T includes adding a precipitation agent to said reaction mass.

5. The process of claim 1 wherein said formic acid is present as at least 85% formic acid in water in an amount insufficient to form a solution with said complex amine and paraformaldehyde.

6. The process of claim 1 wherein said alkylbenzene solvent is selected from the group consisting of toluene, xylenes, trimethylbenzene, and ethylbenzene.

7. The process of claim 1 wherein said complex amine paraformaldehyde, and formic acid are present in an amount such that the molar ratio of >NH groups:HCHO:HCOOH is in the range from about 1:1.02:1.02 to 1:1.1:1.2 and said alkylbenzene is toluene.

8. The process of claim 3 wherein said polysubstituted piperazin-2-one substituent is selected from the group consisting of
1-[3-(isopropylamino)propyl]-3,3,5,5-tetramethylpiperazin-2-one;
1-[2-(isopropylamino)ethyl]-3,3,5,5-tetramethylpiperazin-2-one;
1-[2-(butylamino)ethyl]-3,3,5,5-tetramethylpiperazin-2-one; and,
1-[2-(cyclohexylamino)ethyl]-3,3,5,5-tetramethylpiperazin-2-one; and, said polysubstituted piperazine substituent is selected from the group consisting of
1-[3-(isopropylamino)propyl]-3,3,5,5-tetramethylpiperazine;
1-[2-(isopropylamino)ethyl]-3,3,5,5-tetramethylpiperazine;
1-[2-(butylamino)ethyl]-3,3,5,5-tetramethylpiperazine; and,
1-[2-(cyclohexylamino)ethyl]-3,3,5,5-tetramethylpiperazine.

9. The process of claim 7 wherein there is less than 3% by weight water in said reaction mass after methylation of said triazine compound so that said process is carried out in essentially dry conditions.

10. The process of claim 7 wherein there is less than 30% by weight water in said reaction mass after methylation of said triazine compound so that said process is carried out in wet conditions.

11. The process of claim 10 wherein there is less than 10% by weight water in said reaction mass after methylation of said polysubstituted piperazin-2-one substituent, so that said process is carried out in wet conditions, and steps (a) through (d) completed in less than 8 hr.

12. The process of claim 9 wherein said complex amine has a polysubstituted piperazin-2-one substituent, and is present with said paraformaldehyde, and formic acid in an amount such that the molar ratio of >NH groups:HCHO:HCOOH is in the range from about 1:1.02:1.02 to 1:1.1:1.2 and said alkylbenzene is toluene.

13. The process of claim 9 wherein there is less than 3% by weight water in said reaction mass after methylation of said polysubstituted piperazin-2-one substituent, so that said process is carried out in essentially dry conditions, and steps (a) through (d) are completed in less than 8 hr.

14. The process of claim 6 wherein precipitating said methylated PIP-T includes adding a precipitation agent to the reaction mass.

15. The process of claim 14 wherein said precipitation agent is a liquid $C_5$–$C_{12}$ alkane.

16. The process of claim 15 wherein said complex amine is introduced into the reaction zone as an essentially dry powder, or a solution in toluene, or as a toluene-wet slurry.

17. The process of claim 16 wherein the partition coefficient for said methylated product in a mixture of toluene and water and is about 0.99 so that, upon washing with water, less than 1% of said product is left in the aqueous phase.

18. The process of claim 15 wherein said complex amine is introduced into the reaction zone as a water-wet slurry.

19. The process of claim 18 wherein the partition coefficient for said methylated product in a mixture of toluene and water and is about 0.99 so that, upon washing with water, less than 1% of said product is left in the aqueous phase.

20. In a modified Eschweiler-Clarke process in which an excess of formaldehyde and at least 85% formic acid is used to methylate the NH groups of a complex amine, specifically a triazine ring substituted with at least one polysubstituted piperazine or polysubstituted piperazine-2-one ("PSP") substituent having at least one PSP substituent, each said substituent having a hindered $N^4$ atom flanked either by disubstituted carbon atoms, or carbon atoms having spiro substituents, the improvement comprising, (a) reacting (i) said complex amine with (ii) a solid oligomer of said formaldehyde present as paraformaldehyde, and (iii) said formic acid in amounts such that the molar ratio of NH groups:HCHO:HCOOH is in the range from about 1:1:1 to 1:1.5:1.5 sufficient to methylate at least the >NH group of said PSP substituent if said complex amino also contains terminal —NH groups, so as to obtain essentially quantitative conversion of said PSP substituent to methylated PSP-substituent in said complex amine;

(b) adding a sufficient amount of an alkylbenzene solvent to maintain the reactants in solution, yet upon completion of the reaction, to have less than 3% by weight of water in the solution of methylated product in the reaction mass, (c) maintaining a temperature above about 60° C. but below a temperature at which more than 10% by weight of said complex amine is converted to byproducts, so as to form a solution of methylated complex amine in said alkylbenzene solvent;

(d) neutralizing unreacted formic acid with an aqueous alkaline solution without precipitating methylated product;

(e) separating an aqueous phase of neutralized formic acid from said solution of methylated complex amine present as a solvent phase;

(f) washing said solvent phase with an aqueous wash in which said methylated complex amine is 10 times less soluble than it is in said alkylbenzene solvent so as to wash out water-soluble impurities with said aqueous wash;

(g) adding a liquid $C_5$–$C_{12}$ alkane precipitating agent at a temperature low enough to precipitate a solid mass of said methylated complex amine; and, (h) recovering said methylated product in essentially pure form, in an yield in excess of 90%, said product having a toluene content of less than 1%.

21. The process of claim 20 wherein said complex amine contains terminal —NH groups, said molar ratio of NH groups:HCHO:HCOOH is based on the sum of >NH and terminal —NH groups present in said complex amine; the molar ratio is in the range from about 1:1.02:1.02 to 1:1.1:1.2; and, said alkylbenzene is selected from the group consisting of toluene, xylenes, trimethylbenzene, and ethylbenzene.

22. In a modified Eschweiler-Clarke process in which an excess of formaldehyde and at least 85% formic acid is used to methylate the NH groups of a complex amine, specifically a triazine ring substituted with at least one polysubstituted piperazine or polysubstituted piperazin-2-one ("PSP"), each said substituent having a hindered $N^4$ atom flanked either by disubstituted carbon atoms, or carbon atoms having spiro substituents, the improvement comprising, (a) reacting (i) said complex amine having terminal —NH groups with (ii) a solid oligomer of said formaldehyde present as paraformaldehyde, and (iii) said formic acid in amounts such that the molar ratio of NH groups:HCHO:HCOOH is in the range from about 1:1:1 to 1:1.5:1.5 sufficient to methylate each >NH group of said PSP substituent and at least some of said terminal —NH groups, so as to obtain essentially quantitative conversion of said PSP substituent to methylated PSP-substituent in said complex amine;

(b) adding a sufficient amount of an alkylbenzene solvent to maintain the reactants in solution;

(c) maintaining a temperature above about 60° C. but below a first temperature at which more than 10% by weight of said complex amine is converted to byproducts in a first portion of the reaction so as to form a solution of methylated complex amine in said alkylbenzene solvent;

(d) maintaining a second temperature, sufficiently higher than said first temperature, to produce an effluent of mixed alkylbenzene and water vapors;

(e) separating water from said effluent and returning alkylbenzene solvent to the reaction zone and finishing the reaction at or above said second temperature;

(f) neutralizing unreacted formic acid with an aqueous alkaline solution without precipitating methylated complex amine;

(g) separating an aqueous phase of neutralized formic acid from said solution of methylated complex amine present as a solvent phase;

(h) washing said solvent phase with an aqueous wash in which said methylated complex amine is 10 times less soluble that it is in said alkylbenzene solvent so as to wash out water-soluble impurities with said aqueous wash;

(i) precipitating said methylated complex amine as a solid methylated product from said solvent phase;
(j) drying said methylated product; and,
(k) recovering said methylated product in essentially pure form, in an yield in excess of 90%, said product having a toluene content of less than 1%.

23. The process of claim 22 wherein the number of terminal —NH groups in said complex amine ranges from 2 to 3, and said molar ratio of NH groups:HCHO:HCOOH is based on the sum of >NH and terminal —NH groups present in said complex amine; the molar ratio is in the range from about 1:1.02:1.02 to 1:1.1:1.2; and, said alkylbenzene is selected from the group consisting of toluene, xylenes, trimethylbenzene, and ethylbenzene.

24. The process of claim 23 wherein precipitating said methylated product from said solvent phase is effected by adding a sufficient amount of liquid $C_5$–$C_{12}$ alkane precipitating agent at a temperature low enough to precipitate a solid mass of said methylated complex amine.

* * * * *